(12) United States Patent
Strahm et al.

(10) Patent No.: US 6,534,005 B1
(45) Date of Patent: Mar. 18, 2003

(54) PHASE TRANSITION ANALYZER

(75) Inventors: Bradley S. Strahm, Sabetha, KS (US); Brian S. Plattner, Sabetha, KS (US)

(73) Assignee: Wenger Manufacturing, Inc., Sabetha, KS (US)

( * ) Notice: Subject to any disclaimer, the term of this patent is extended or adjusted under 35 U.S.C. 154(b) by 24 days.

(21) Appl. No.: 09/812,180

(22) Filed: Mar. 19, 2001

(51) Int. Cl.$^7$ .............................................. G01N 25/20
(52) U.S. Cl. ...................................... 422/51; 422/68.1
(58) Field of Search ................................. 422/51, 68.1

(56) References Cited

PUBLICATIONS

Zhang et al. Capillary Rheometry of Corn Endosperm: Glass Transition, Flow Properties, and Melting of Starch; *Cereal Chemistry*, 65(6):863–867.
Strahm; Fundamentals of Polymers Science as an Applied Extrusion Tool; *Cereal Foods World*; 43(8):621–625 (1988).
Zhang et al.; Affecting Expansion of Corn Meals with Poor and Good Expansion Properties; *Cereal Chemistry*; 75(5):639–643 (1998).

*Primary Examiner*—Jill Warden
*Assistant Examiner*—Sam P. Siefke
(74) *Attorney, Agent, or Firm*—Hovey Williams LLP

(57) ABSTRACT

An improved phase transition analyzer (22) is provided which greatly facilitates analysis of composite mixtures such as protein and starch-containing extrudate mixtures to give valuable information about the mixture, e.g., glass transition and melt transition temperatures, $T_g$ and $T_m$. The analyzer (22) includes a body (74) having a chamber (192) adapted to receive a sample (196) of a material to be analyzed, together with a force-applying assembly (34–40, 68) operable to apply a compressive force to the sample 196 and a heating assembly (96, 138). In order to determine $T_g$, the sample (196) is progressively heated under sustained exertion of compaction force with chamber (192) closed. The sample (196) is compacted and the volume of chamber (192) correspondingly decreases, this being sensed by movement of a portion (34, 36) of the force-applying assembly (34–40, 68) by a displacement transducer (44). To measure $T_m$, the block (38) is moved to a second position providing a capillary escape opening (162) at the chamber (192). Continued progressive heating of the sample (196) under compressive force causes the sample (196) to melt and flow through opening (162). The consequent movement of the portion (34, 36) is again sensed by transducer (44).

29 Claims, 7 Drawing Sheets

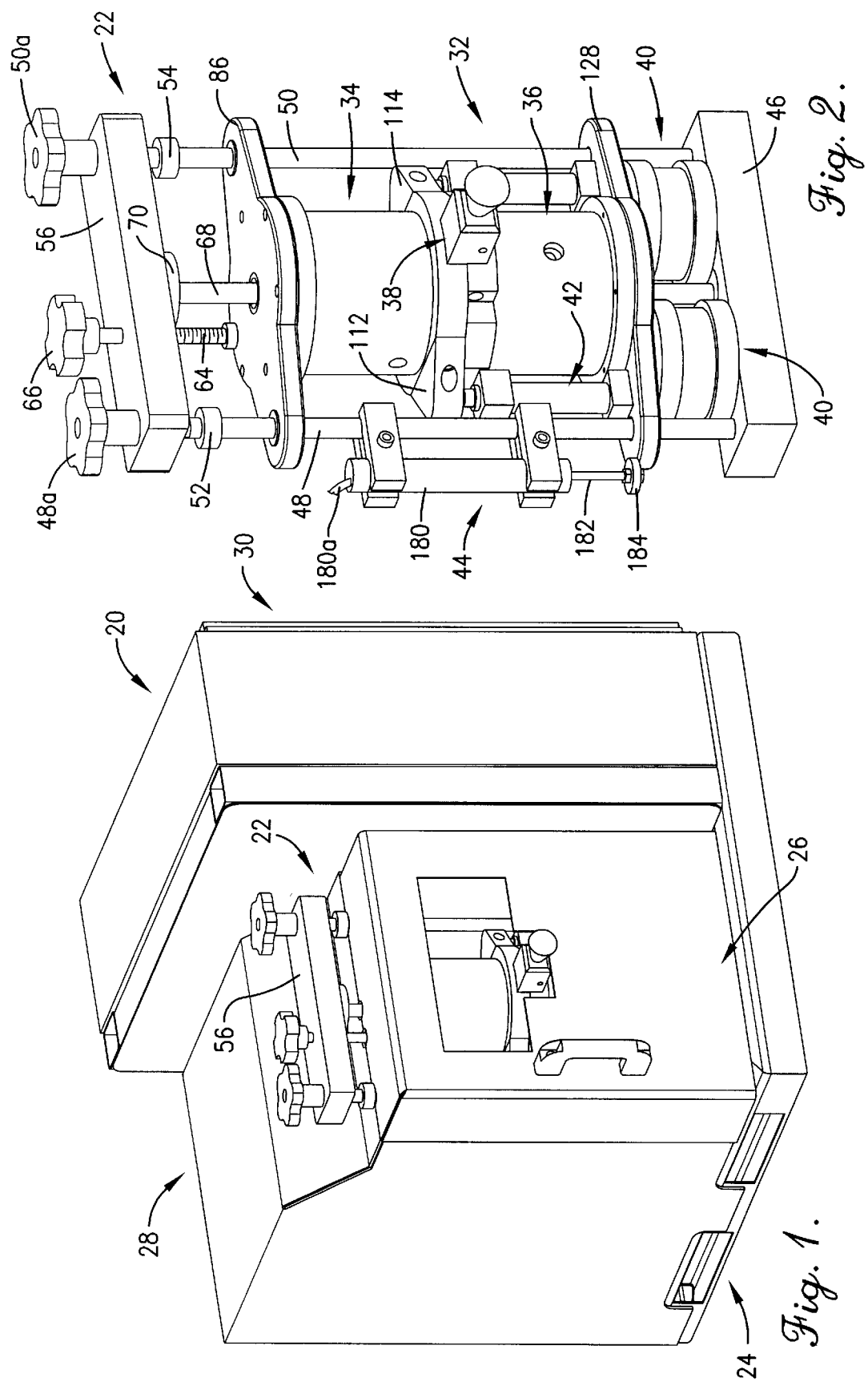

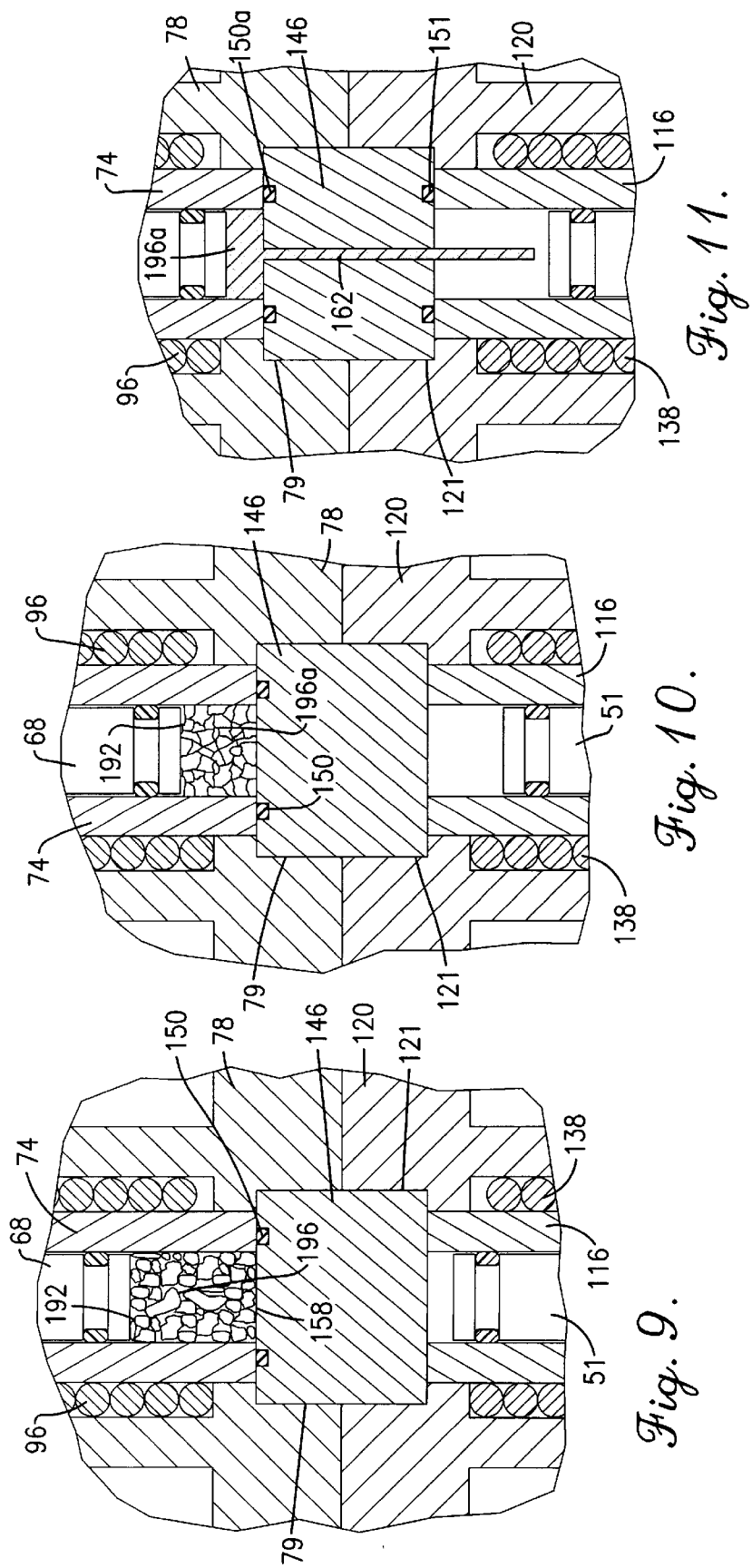

PHASE TRANSITION ANALYZER

BACKGROUND OF THE INVENTION

1. Field of the Invention

A CD-ROM containing a computer program listing appendix has been submitted. The CD-ROM contains 1 dick, containing a total of 218 files.

The present invention is broadly concerned with an improved material transition analyzer and method permitting analysis of non-uniform, composite materials in order to determine temperature-related phases of material, such as the glass transition temperature ($T_g$) and melt transition temperature ($T_m$). More particularly, the invention is concerned with such analyzer and method wherein the analyzer includes a body having a sample chamber, a sample heating assembly, and a force-applying assembly operable to apply a compressive force to the sample which decreases the chamber volume in response to sample phase changes; the change in volume is detected, preferably by monitoring corresponding shifting of a portion of the force-applying assembly.

2. Description of the Prior Art

Thermal processing techniques such as extrusion and pelleting generate complex chemical and physical changes in ingredients to produce final products with desired characteristics. Modern instruments and analytical tools can measure these often minute but critical changes. By correlating these changes to desired properties in finished products, it is possible to predict processing effects and to more accurately formulate diets and automated processing parameters.

A relatively new approach that is rapidly increasing in popularity is the application of polymer science to extrusion and similar technologies. Having roots in the plastic polymer industry, polymer science can be used to study the physical changes associated with glass transition and melt transition in biopolymers such as starches and proteins. In order to make use of the principles of polymer science, it is first important to recognize the difference between the crystalline physical state and the amorphous (noncrystalline state). In basic terms, if the polymers in a substance become very ordered, they interact with one another and form a crystalline structure. In amorphous materials, adjacent strands of the polymer do not interact with one another and, therefore, do not crystallize. It is important to understand that the principles of polymer science apply only to amorphous materials.

Both synthetic and food polymers often exist in an amorphous or partially amorphous state. These amorphous compounds undergo both glass transition and melting at characteristic temperatures $T_g$ and $T_m$, respectively. When the temperature of the compound is above $T_g$ but below $T_m$, it is easily deformed but is not so liquid-like that it flows, and the compound is considered "rubbery" or leathery.

An example of a rubbery material is a food product as it exits an extruder before cooling and drying. At this point in the process, the crystalline starch structure has been destroyed, and the mass is amorphous. When grasped by hand, the product can be easily deformed without fracturing the structure, yet it is sufficiently coherent that it will not flow through one's fingers.

When the temperature of a compound is below $T_g$, it is considered "glassy". An example of a glassy material is an extruded food product after it has been dried or, in some cases, only cooled. At this point, the structure is amorphous, and when deformed with one's fingers, the structure fractures.

When the temperature of a compound is above $T_m$, its properties are fluid-like, and the compound is considered "melted." An example of a melted material is extrudate that is heated and plasticized sufficiently to flow through the extruder die.

Important changes in the physical properties of polymers occur as they pass through their glass transition temperatures. The most notable changes occur in molecular mobility, viscosity, and elasticity.

In the rubbery state, molecular mobility, indicated by the material's viscosity, is much, much greater than in the glassy state. Therefore, in the rubbery state, viscosity is much, much lower than in the glassy state. For example, the viscosity of a glassy material may be in the range of $10^{12}$ Pa while the corresponding viscosity of the same material in the rubbery state would be several orders of magnitude less. Similarly, several order-of-magnitude differences in viscosity can be seen between the rubbery state ($T_m<T<T_g$) and the melted state ($T>T_m$). See, Zhang et al., Factors Affecting Expansion of Corn Meals with Poor and Good Expansion Properties, *Cereal Chemistry*, Vol. 75, No. 5, (1998); and Strahm, Fundamentals of Polymer Science as an Applied Extrusion Tool, *Cereal Foods World*, Vol 43, No. 8, (1998).

Devices have been proposed in the past to measure the properties of grain products at or near the pressures and temperatures encountered in high-temperature short-time extrusion, Zhang et al., Capillary Rheometry of Corn Endosperm: Glass Transition, Flow Properties, and Melting of Starch, *Cereal Chemistry*, Vol. 75, No. 6, (1998). The Zhang et al. device makes use of a capillary block with opposed, constant volume chambers on opposite sides of the block. Each chamber contained a piston which were moved together through sidebars ensuring that the volume of the chambers remained constant while preventing moisture loss through the atmosphere.

SUMMARY OF THE INVENTION

The present invention provides an improved phase transition analyzer comprising a body having a chamber presenting an open end and adapted to receive a material sample, together with a heating assembly for controllably heating a sample within the chamber and a force-applying assembly operable to apply a compressive force to the sample with the chamber during heating thereof. The force-applying assembly includes a block adjacent the open end of the body which at least substantially closes the chamber to inhibit flow of the sample therefrom. The force-applying assembly is operable to decrease the volume of the chamber in response to changes in the sample arising from heating and application of force thereto. A device is also provided to determine the decrease in volume of the chamber, which is used to denote a material phase change. In preferred forms, a portion of the force-applying assembly is shiftable in response to changes in the sample, and the device determines the shifting of the force-applying assembly portion.

In preferred forms, the analyzer body comprises an elongated, tubular member which receives an elongated stationary rod, and the block is coupled with a drive unit for urging the block in a direction to compress the sample between the block and the inner end of the rod. In this way, the material sample is subjected to heating and compaction forces so that, when a phase change occurs, the volume of the sample chamber is decreased and detected.

In order to most easily analyze for $T_g$ and $T_m$, the block is preferably a shiftable member having a solid or blank portion and a spaced second portion provided with a capillary opening therethrough. In use, a sample is loaded into the chamber, with the latter closed in its first position, and a compressive force is exerted on the sample while the latter is heated at a predetermined rate; when the material reaches its $T_g$, the sample contracts and the chamber volume correspondingly decreases, the latter being detected. Thereafter in order to measure $T_m$, the block is shifted to its second position and the sample is again heated while being subjected to a compressive force. When the $T_m$ is reached, a portion of the sample flows through the block capillary opening, again causing a detectable decrease in chamber volume.

BRIEF DESCRIPTION OF THE DRAWINGS

FIG. 1 is a perspective view of a phase transition analyzer unit in accordance with the invention;

FIG. 2 is a perspective view of the analyzer assembly of the unit shown in FIG. 1;

FIG. 9 is an enlarged, fragmentary vertical sectional view illustrating the configuration of the analyzer with a material sample loaded therein and prior to initiation of an analysis cycle;

FIG. 10 is a view similar to that of FIG. 9 but showing the analyzer configuration at the time the material sample is heated to its glass transition temperature;

FIG. 11 is a view similar to that of FIG. 10, but showing the analyzer configuration during a melt transition analysis;

DETAILED DESCRIPTION OF THE PREFERRED EMBODIMENT

Figure 3:
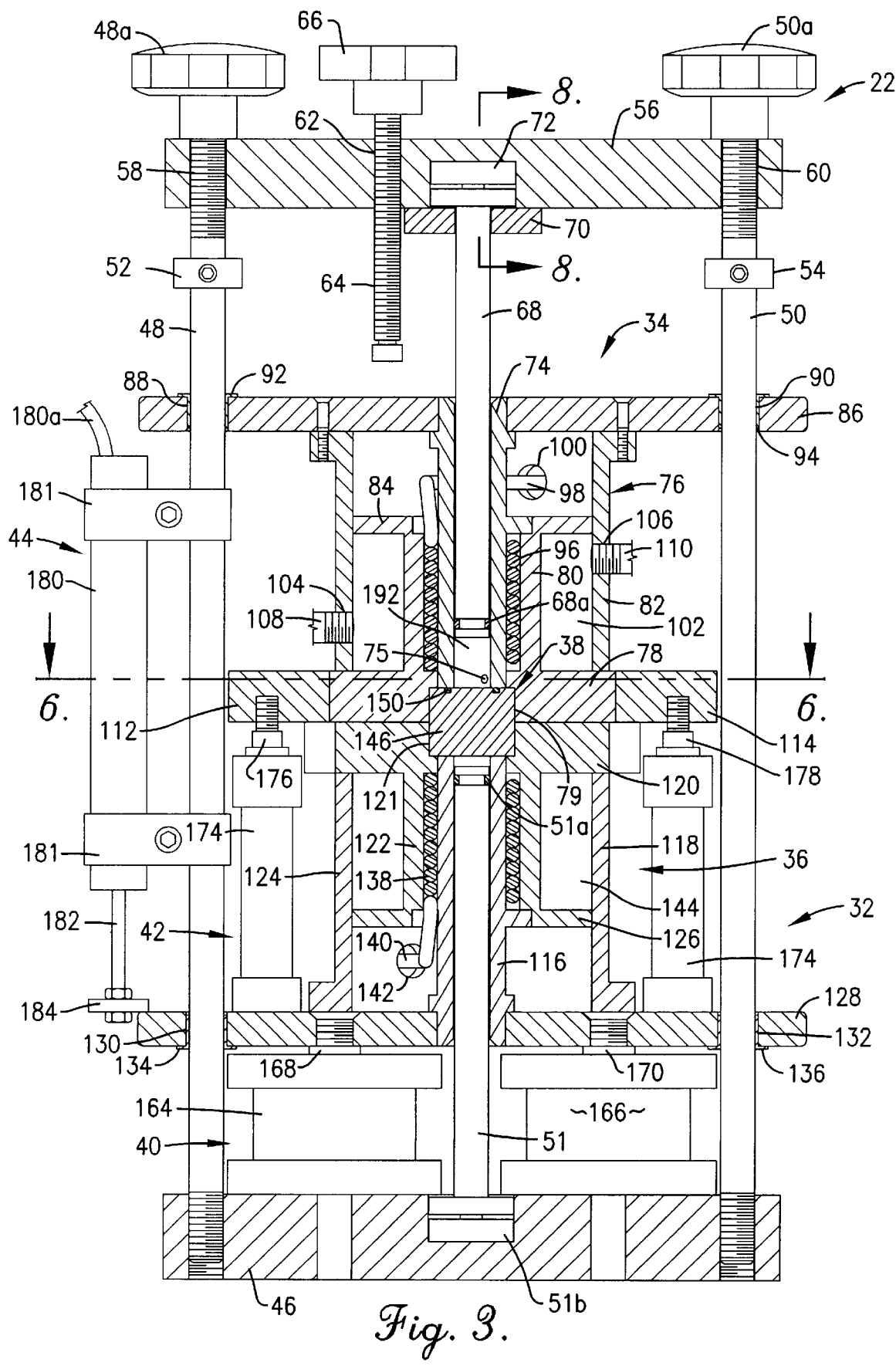
FIG. 3 is a is a vertical sectional view of the analyzer shown in FIG. 2, prior to loading of the analyzer with a sample.

Turning now to the drawings, a preferred phase transition analyzer unit 20 is illustrated in FIG. 1. The unit 20 broadly includes an analyzer 22, cabinetry 24 supporting the latter and having an access door 26; the cabinetry 24 also supports a reservoir assembly 28 and a control circuitry housing 30. The analyzer 22 generally includes a frame assembly 32, upper and lower chambers 34, 36, a shiftable capillary die block 38, sample compaction cylinders 40, chamber separation cylinders 42 and a displacement transducer 44.

Figure 8:
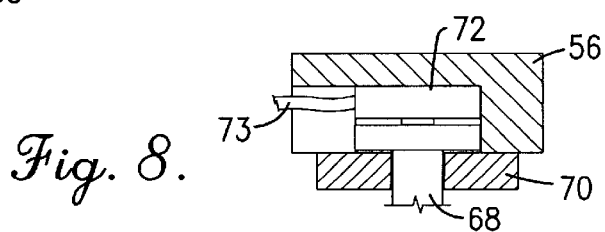
FIG. 8 is a fragmentary sectional view showing the location of one of the load cells of the analyzer.

In more detail, and referring particularly to FIGS. 2 and 3, the frame assembly 32 includes a base 46 which rests within cabinetry 24, a pair of upstanding tie rods 48 and 50 secured to the base 46, as well as a central, upstanding, stationary guide rod 51. The rod 51 has an upper sealing ring 51a and may be equipped with a load cell 51b. Each of the rods 48, 50 has a threaded uppermost end and a stop collar 52, 54 below the upper threading. Assembly 32 also includes a top plate 56 having a pair of through bores 58, 60 permitting passage of the upper ends of the tie rods 48, 50 therethrough; each tie rod is equipped with an uppermost threaded knob 48a, 50a as shown. The plate 56 also has a threaded bore 62 at the central region thereof, which receives an elongated, threaded stop rod 64 provided with handle 66. Although not forming a part of the frame assembly, it will be observed that the plate 56 supports an elongated, depending compaction rod 68 with a lower sealing ring 68a, the rod 68 secured in place via an annular retainer ring 70 attached by screws to the underside of plate 56. In addition, a load cell 72 is mounted within top plate 56 and has a lead 73 (FIG. 8), for purposes to be described.

The upper chamber 34 includes an elongated tubular sleeve 74 which receives the lower end of rod 68 and has a lower, transverse thermocouple-receiving opening 75 formed therethrough. The sleeve 74 is supported by a chamber body 76, made up of bottom wall 78 having a central recess 79, inner annular wall 80, outer annular wall 82 and intermediate lateral wall 84. The outer annular wall 82 is secured to an uppermost apertured crosspiece 86. Note that the crosspiece 86 is provided with two openings 88, 90 therethrough, which are equipped with slide bearings 92, 94; the tie rods 48, 50 extend through the bearings 92, 94 so as to support crosspiece 86 and thus the remainder of chamber 34 for reciprocal up and down movement.

The upper chamber 34 is equipped with temperature maintenance and control apparatus in the form of an electrical resistance heater rope 96 wrapped about sleeve 74 between the latter and inner annular wall 80. The lead 98 of the heater rope 96 passes through an opening 100 in wall 82 and is coupled with a conventional power source (not shown). Additional temperature control is provided by virtue of the annular passageway 102 defined between inner and outer annular walls 80, 82. This passageway permits circulation of heating and/or cooling media, and for this purpose the wall 82 is provided with openings 104, 106 equipped with fluid inlet and outlet conduits 108, 110.

A pair of connection ears 112, 114 are secured in opposed relationship to bottom wall 78 of chamber 34. These ears in effect define lateral projections from the bottom wall 78 and are important for purposes to be described. Also, an elongated lateral bore 107 (FIG. 7) is provided through the bottom wall 78 and is in registry with sleeve opening 75.

Lower chamber 36 is disposed directly below upper chamber 34 and essentially coaxial therewith. The lower chamber 36 has a tubular sleeve 116 which is slidably received on guide rod 51. The sleeve 116 is coupled with a chamber body 118 made up of an upper wall 120 having a central recess 121, inner and outer annular walls 122, 124, and intermediate lateral wall 126. The lower body chamber 36 is secured to a lower crosspiece 128 which is very similar to the crosspiece 86. Specifically, crosspiece 128 has a pair of apertures 130, 132 therethrough with slide bearings 134, 136 seated therein. These bearings slidably receive the tie rods 48, 50.

The lower chamber 36 has an electrical resistance heater rope 138 coiled about sleeve 116 between the latter and annular wall 122. The heater rope 138 has a lead 140 which passes through opening 142 in wall 18 to afford a power connection. Additional temperature maintenance and control is provided by annular passageway 144 defined between inner and outer walls 122, 124. As in the case of the passageway 102 of the upper chamber, appropriate inlet and outlet openings and conduits are provided to permit circulation of heating and/or cooling medium through the passageway 144.

The capillary die block 38 (see FIG. 6) is in the form of an elongated, rectangular in cross-section block 146 having an outer manipulation handle 148. The block 146 has a pair of spaced apart upper sealing rings 150, 150a, as well as a lower sealing ring 151, and is designed to fit between the upper and lower chambers 34, 36 within the mated recesses 79, 121 of the latter. In this orientation, the upper surface of the block 146 engages the butt end of upper sleeve 74. Similarly, the lower face of block 146 directly engages the upper butt end of sleeve 116. The side face of block 146 has a pair of spaced apart detent openings 152, 154 therein which mate with a spring loaded detent 156 provided in bottom wall 78 of upper chamber 34 (see FIG. 6).

The block 146 presents two operative segments which can be alternately positioned between the sleeves 74, 116 as will be described. The first segment 158 (FIG. 7) is a "blank" segment, meaning that it has no opening therethrough, with the sealing ring 150 surrounding this segment. The second segment 160 on the other hand is provided with a narrow capillary passage 162, and has upper and lower sealing rings 150a and 151 disposed about this second segment.

The sample compaction cylinders 40 are in the form of conventional pneumatic pancake cylinders 164, 166 secured to the upper face of base 46. Each of the cylinders 164, 166 includes an extensible piston rod 168, 170 connected to crosspiece 128.

Figure 6:
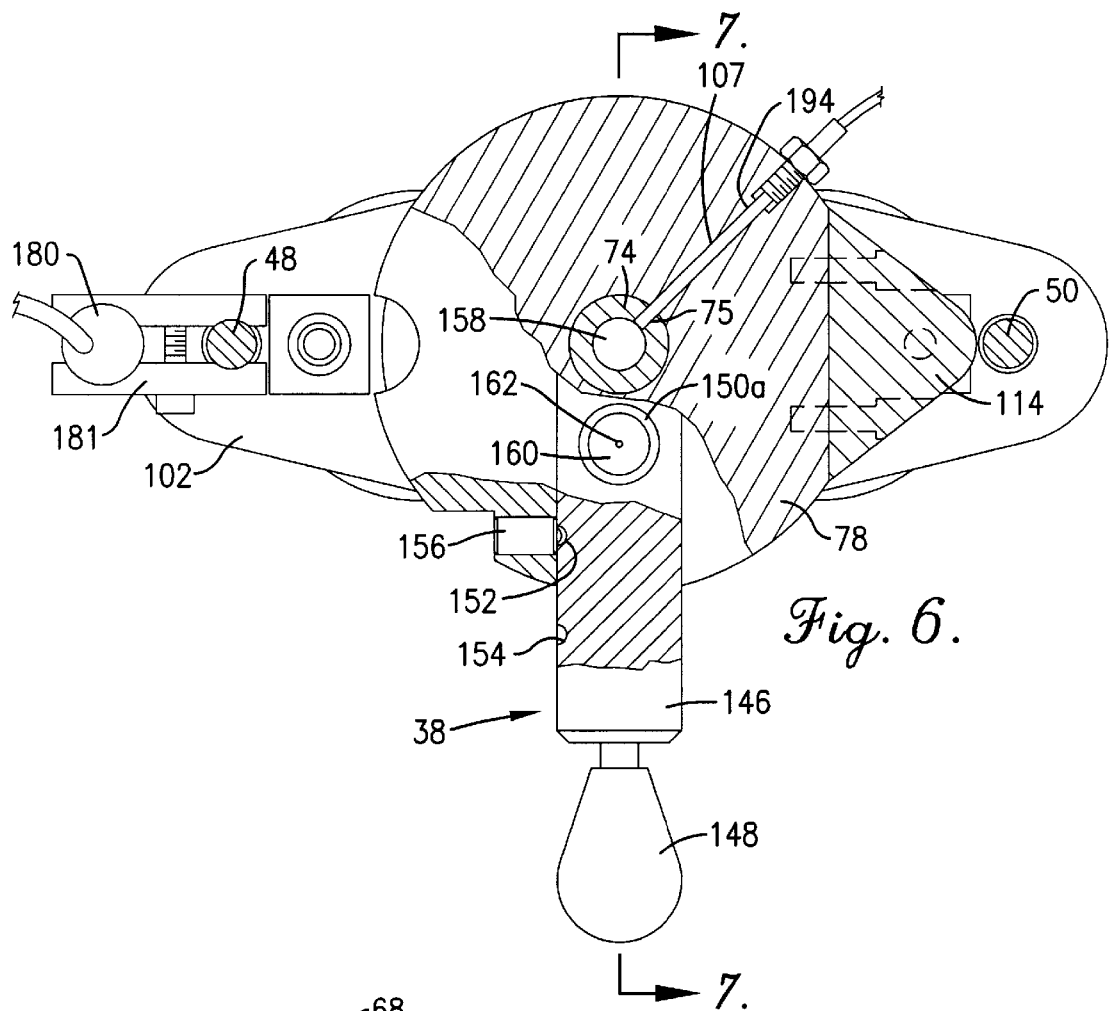
FIG. 6 is a sectional view with parts broken away taken along lines 6—6 of FIG. 3.

The chamber separation cylinders 42 are also pneumatically activated and include upright cylinders 172, 174 secured to crosspiece 128 on opposite sides of lower chamber 36 and having extensible rods 176, 178. As illustrated in FIGS. 3 and 6, the rods 176, 178 are respectively secured to the ears 112, 114.

The displacement transducer 44 comprises an elongated transducer body 180 having lead 180a and secured to tie rod 48 by way of couplers 181 and having a depending, shiftable probe 182. The lower end of probe 182 has a radially enlarged engagement element 184 which rests atop crosspiece 128.

Figure 12:
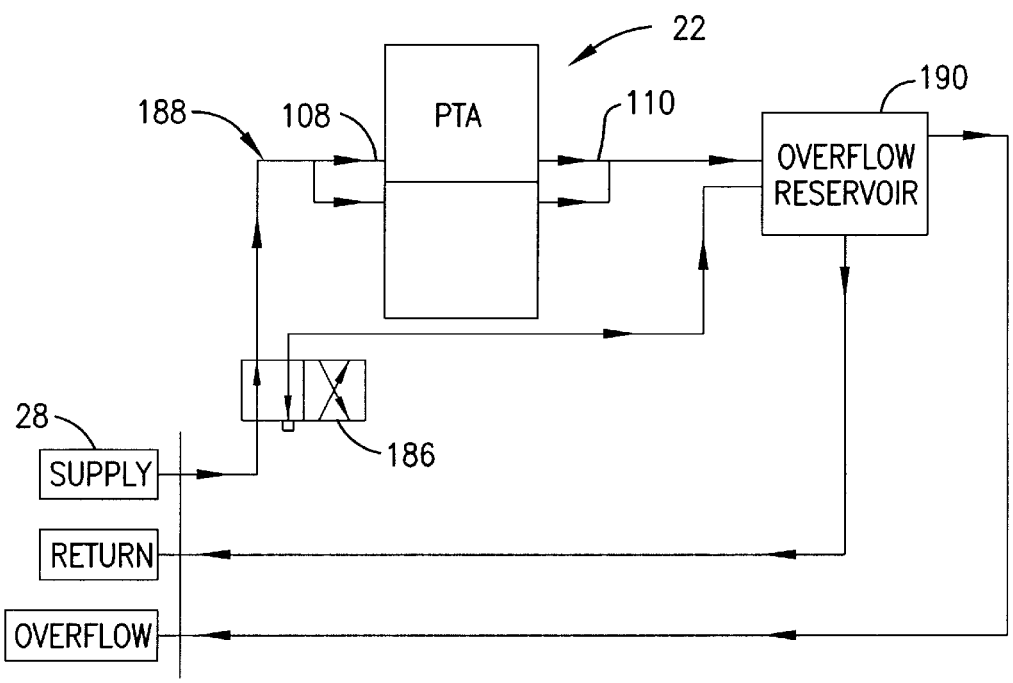
FIG. 12 is a schematic representation of the coolant circulation system used in the preferred phase transition analyzer.

In preferred operation, the analyzer 22 is provided with a fluid cooling medium which is circulated through the annular passageways 102 and 144. To this end (FIG. 12), a supply of such coolant is located within reservoir or supply 28 and is connected via conventional valving 186 and conduit system 188 to the input and output conduits 108, 110 associated with the upper and lower chambers 34, 36. An overflow reservoir 190 is also a part of the coolant circuit, together with return and overflow ports as shown.

FIG. 3 illustrates analyzer 22 where blank block segment 158 is positioned beneath sleeve 74. In this orientation, it will be observed that a sample chamber 192 is defined by the annular sidewall of sleeve 74, the lower surface of rod 68 and the upper surface of block 146, specifically the surface of first segment 158. This closed chamber 192 is sealed by virtue of the engagement of sealing ring 158 with the butt lower end of sleeve 74.

The analyzer unit 20 is especially designed for measurement of glass transition and melt transition temperatures $T_g$ and $T_m$ of a selected composition such as an extrudable mixture. In setting up the analyzer unit, a personal computer loaded with the appropriate control software is operatively coupled with the conventional electronics located within circuitry housing 30. Also, the analyzer 22 is opened to permit loading of a material sample 196 within the sleeve 74. This is accomplished by first detaching the knobs 48a, 50a from the tie rods 48, 50 and removing top plate 56 from the analyzer.

Figure 7:
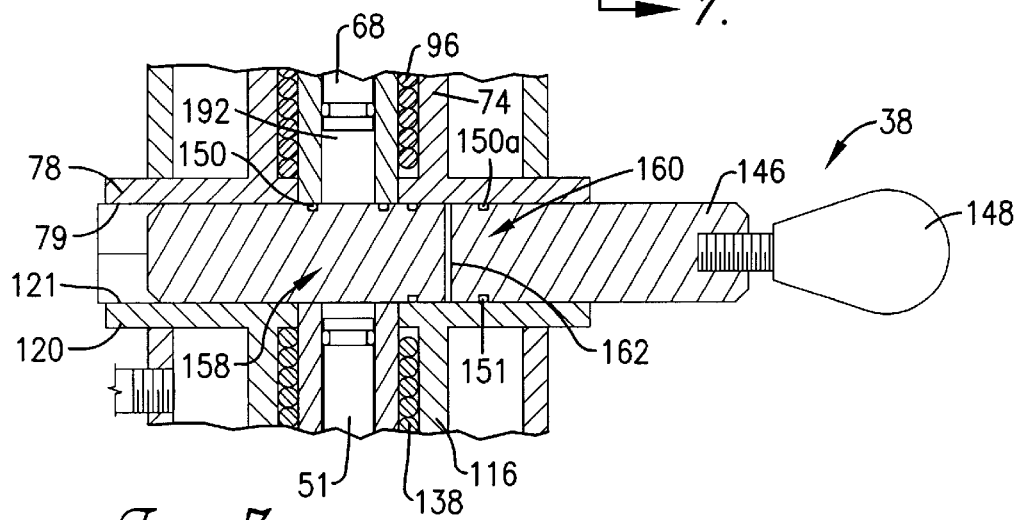
FIG. 7 is an enlarged, fragmentary sectional view illustrating the first position of the capillary block forming a part of the analyzer.

The first segment 158 of block 38 is positioned within the recesses 79, 121 in blocking relationship to the open lower end of sleeve 74. The sample 196 (e.g., 1.5 g) of the mixture to be analyzed is then placed within the sleeve 74 so that it rests atop the upper surface of the segment 158. Next, the top plate 56 is reinstalled, by telescoping rod 68 into sleeve 74 and passing the tie rods 48, 50 through the top plate bores 58, 60. Rod 64 is also adjusted to define the upper limit of travel of the chambers 34, 36. FIG. 9 illustrates the apparatus in this initial state. The necessary sensors including load cell 72 and transducer 180, and a thermocouple 194 (which is positioned within the bore 109 and opening 75 as best seen in FIG. 7), are coupled with the control electronics in housing 20.

Figure 4:
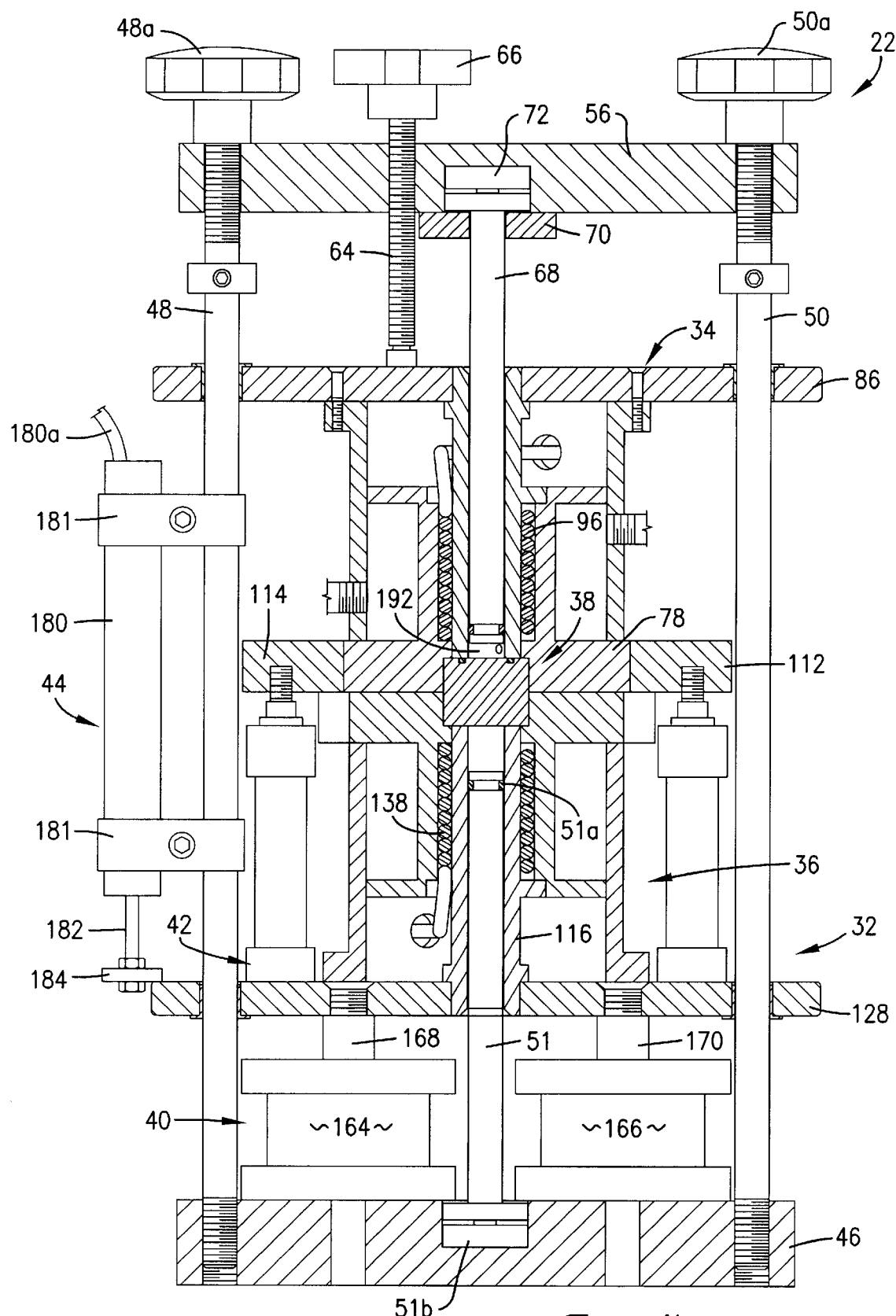
FIG. 4 is a vertical sectional view similar to that of FIG. 3, but depicting the apparatus at the conclusion of a glass transition temperature analysis.

In order to measure the $T_g$ of the sample, the pancake cylinders 164, 166 are actuated to extend the rods 168, 170 as shown in FIG. 4. This serves to elevate crosspieces 128 and 86, causing the upper and lower chambers 34, 36 to move upwardly relative to stationary rod 68. As a consequence, a compressive force is exerted on the sample within chamber 192 by an assembly comprising cylinders 40, crosspiece 128, lower chamber 34, upper chamber 36, block 38 and rod 68. Preferably, during the glass transition analysis the force exerted on the sample is at a predetermined constant level. During such application of force, the heating assembly including the resistance heaters 96, 138 is actuated to heat the sample at a controlled rate, for example 10° C. per minute. As the sample 196 softens and moves through its glass transition stage, it compacts to a smaller volume sample 196a depicted in FIG. 10. This compaction and the resultant decrease in volume of the chamber 192 is sensed by the transducer 44. In particular, as the volume of chamber 192 decreases as a consequence of the material moving through its glass transition stage, the crosspiece 128 moves upwardly, thereby shifting probe 182 upwardly. This movement of the transducer probe signals that the glass transition temperature has been reached.

If it is then desired to measure the melt transition temperature of the sample 196, the following steps are followed. First, the resistant heating elements 96, 138 are shut down and coolant is circulated through the passageways 102, 144 in order to cool the sample. Also, the separation cylinders 42 are actuated to very slightly move upper chamber 34 relative to lower section 36. This allows sliding movement of the block 38, which is accomplished manually by grasping handle 148 and pushing the block 146 against the bias of detent 156, until the bar is moved past detent opening 152 and seats within opening 154. In this orientation, the second segment 160 is positioned between the sleeves 74 and 116 as illustrated in FIG. 11. The cylinders 42 are then retracted to securely lock the bar 149 in place. At this point, circulation of cooling fluid is stopped and the heating elements are reactivated so as to increase the sample temperature at a controlled rate, again typically 10° C. per minute. This is continued until the sample 196a is sufficiently melted to permit flow of sample through the capillary opening 162 and into the open space below block 146. Again, this results in a further decrease in the volume of sample chamber 192, this being detected by upward movement of the crosspiece 128 by transducer 44.

While this general procedure is followed to determine $T_g$ and $T_m$, it is subject to many variations. Thus, it may be desirable to initially compact the sample 196 within chamber 192 (e.g. to 100 bars) to a point where the first controlled heating step to determine $T_g$ is initiated. The illustrative times and temperature rates given above can also be varied over a wide range, principally dependent upon the type of sample being measured.

Figure 13:
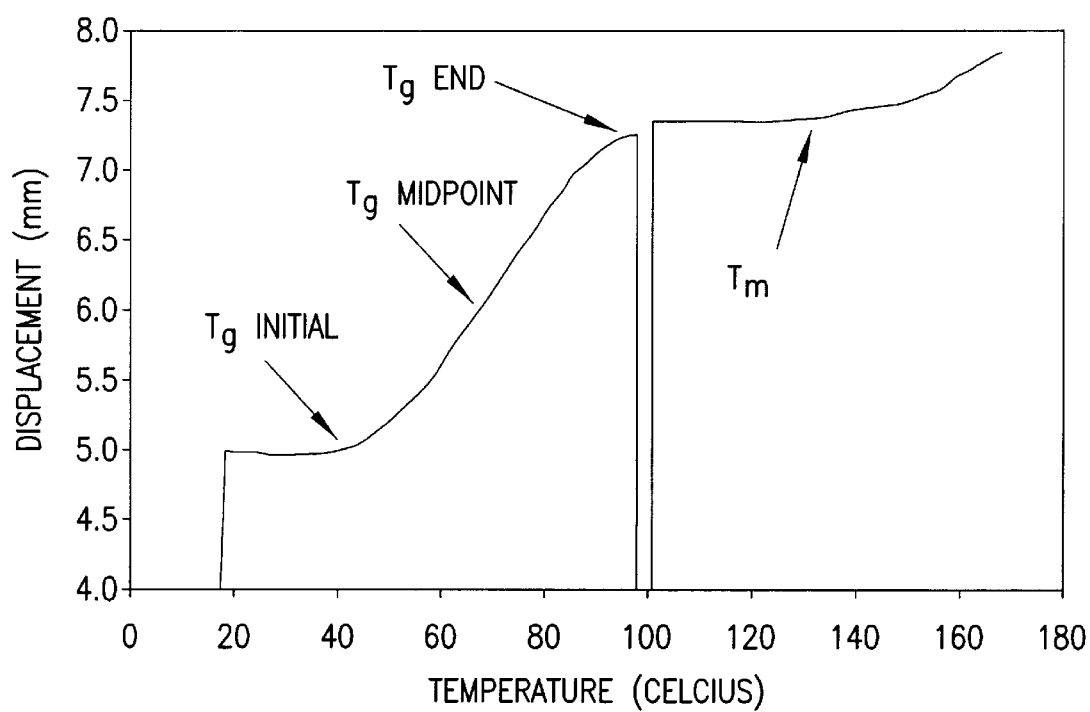
FIG. 13 is a typical displacement/temperature graph generated by the analyzer of the invention to establish the glass transition and melt transition temperatures for a sample.

FIG. 13 depicts a typical graph developed using the analyzer unit 20. Displacement is tracked as the sample is heated, with glass transition indicated by sample compaction and resultant decrease in the volume of sample chamber 192. The glass transition usually occurs over a temperature range as show, $T_g$ initial and $T_g$ end. The melt transition $T_m$, occurring when the sample flows through capillary opening 162 (FIG. 11) is also tracked by the displacement transducer 180.

The unit 20 is also capable of further analyses. If it is desired to measure sample viscosity, use can be made of optional lower load cell 51b below rod 51. In such analyses, after passage through the capillary opening 162, the material is collected within the lower secondary chamber between the upper end of rod 51 and the lower surface of block 146.

Figure 5:
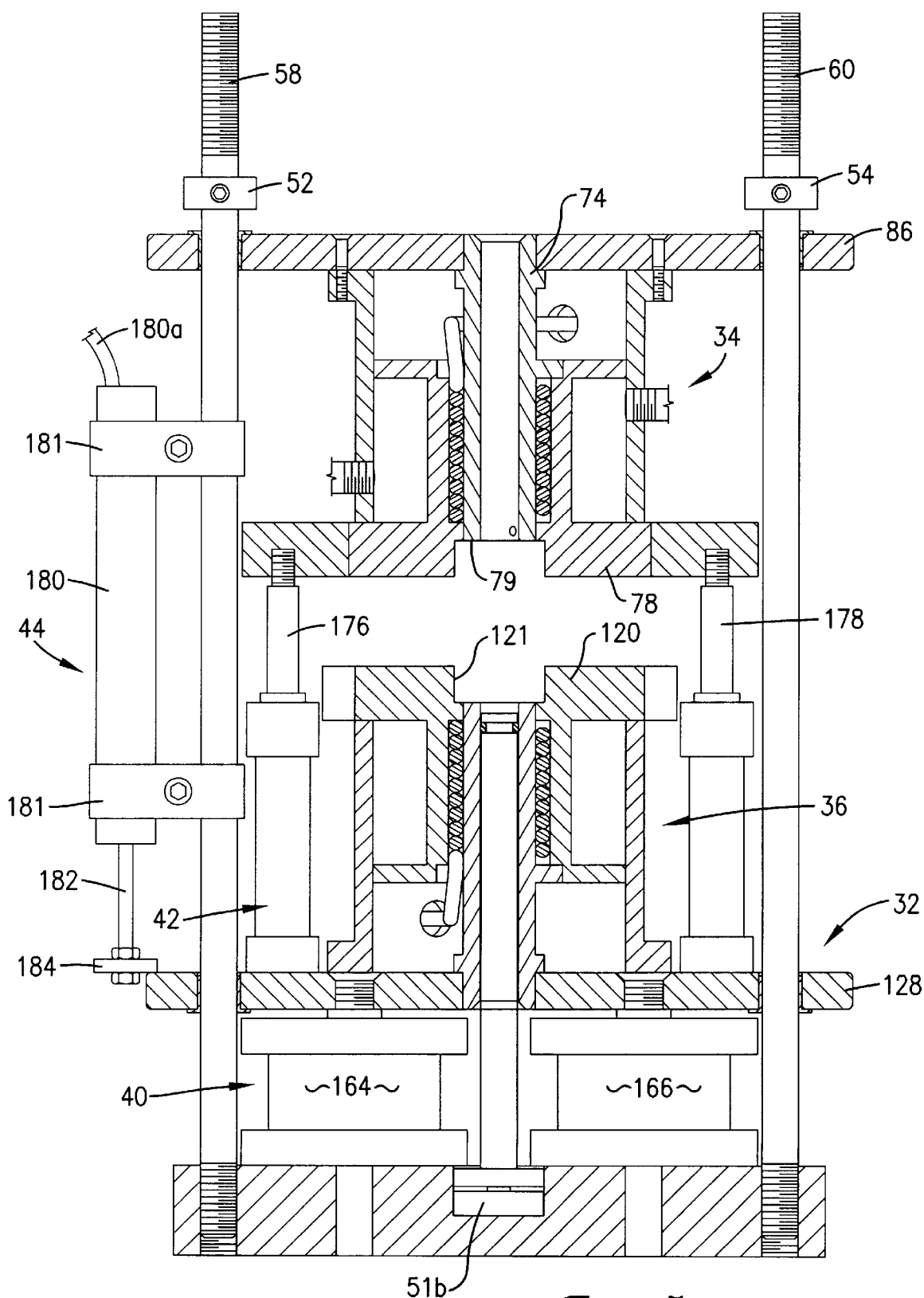
FIG. 5 is a vertical sectional view of the apparatus shown in FIGS. 3 and 4, but depicting the apparatus in its opened, clean-out position.

FIG. 5 illustrates the configuration of the analyzer 22 in the fully opened, cleanup position. In this case, the knobs 48a, 50a are removed, and top plate 56 is slid off the tie rods 48, 50. The cylinders 42 are then operated to extend rods 176, 178 to their maximum extent which fully separates the chambers 34 and 36. This allows removal of block 38 and access to the components of the analyzer 22 for cleanup and repair.

The preferred control software resident on the personal computer (not shown) coupled with the unit 20 is presented in the source code appendix incorporated by reference herein.

All documents cited are incorporated by reference herein. We claim:

1. A material phase transition analyzer, comprising:
    a body having a chamber presenting an open end and adapted to receive a sample of material to be analyzed;
    a heating assembly operable to controllably heat said sample within said chamber;
    a force-applying assembly operable to apply a compressive force to said sample within the chamber, including a block adjacent said body open end which at least substantially closes said chamber so as to inhibit flow of said sample therefrom said block having a first solid segment positionable across said open end to prevent escape of said sample from said chamber during said heating and application of force to said sample, and a second apertured segment alternately positionable across said open end to only partially close the open end to permit limited escape of said sample from said chamber;
    said force-applying assembly operable to decrease the volume of said chamber in response to changes in said sample arising from said heating and application of force thereto; and
    a device operable to determine said decrease in volume of said chamber.

2. The analyzer of claim 1, said body comprising a tubular member presenting said open end.

3. The analyzer of claim 2, said force-applying assembly comprising:
    an elongated, stationary rod received within said tubular member, the end of said rod remote from said open end defining one end of said chamber spaced from said open end; and
    a drive unit operably coupled with said block for urging said block in a direction to compress said sample between the block and said rod end.

4. The analyzer of claim 3, said drive unit comprising a pair of piston and cylinder assemblies.

5. The analyzer of claim 3, said force-applying assembly further comprising:
    an elongated guide rod in axial alignment with said stationary rod, with said block positioned between the guide rod and stationary rod; and
    an element mounted on said guide rod and axially movable along the length thereof, said element engaging said block, said drive unit coupled with said element.

6. The analyzer of claim 1, a portion of said force-applying assembly be shiftable in response to said decrease in volume of said chamber, said device operable to measure said shifting.

7. The analyzer of claim 6, said device comprising a displacement transducer.

8. The analyzer of claim 1, said heating assembly comprising a resistance heater adjacent said body.

9. The analyzer of claim 8, said heating assembly further including a passageway for circulation of heating or cooling media.

10. The analyzer of claim 1, said block being selectively shiftable so as to selectively and alternately locate either said first or second segments thereof across said open end.

11. A material phase transition analyzer, comprising:
    a body having a chamber presenting an open end and adapted to receive a sample of material to be analyzed;
    a heating assembly operable to controllably heat said sample within said chamber;
    a force-applying assembly operable to apply a compressive force to said sample within the chamber, including a block adjacent said body open end at least substantially closes said chamber so as to inhibit flow of said sample therefrom,
    a portion of said force-applying assembly being shiftable in response to changes in said sample arising from said heating and application of force thereto; and
    a device operable to determine said shifting of said force-applying assembly portion.

12. The analyzer of claim 11, said body comprising a tubular member presenting said open end.

13. The analyzer of claim 12, said force-applying assembly comprising:
    an elongated, stationary rod received within said tubular member, the end of said rod remote from said open end defining one end of said chamber spaced from said open end; and
    a drive unit operably coupled with said block for urging said block in a direction to compress said sample between the block and said rod end.

14. The analyzer of claim 13, said drive unit comprising a pair of piston and cylinder assemblies.

15. The analyzer of claim 13, said force-applying assembly further comprising:
    an elongated guide rod in axial alignment with said stationary rod, with said block positioned between the guide rod and stationary rod; and
    an element mounted on said guide rod and axially movable along the length thereof, said element engaging said block, said drive unit coupled with said element.

16. The analyzer of claim 11, said device comprising a displacement transducer.

17. The analyzer of claim 11, said heating assembly comprising a resistance heater adjacent said body.

18. The analyzer of claim 17, said heating assembly further including a passageway for circulation of heating or cooling media.

19. The analyzer of claim 11, said block having a first solid segment positionable across said open end to prevent escape of said sample from said chamber during said heating and application of force to said sample, and a second apertured segment alternately positionable across said open end to only partially close the open end to permit limited escape of said sample from said chamber.

20. The analyzer of claim 19, said block being selectively shiftable so as to selectively and alternately locate either said first or second segments thereof across said open end.

21. A material phase transition analyzer, comprising:

a body having a chamber presenting an open end and adapted to receive a sample of material to be analyzed;

a heating assembly operable to controllably heat said sample within said chamber;

a force-applying assembly operable to apply a compressive force to said sample within the chamber, including a block adjacent said body open end, said block including a first segment positionable across said open end to close said chamber and prevent escape of said sample during said heating and application of force thereto, and a second apertured segment alternately positionable across said open end to only partially close the chamber to permit limited escape of said sample during heating and application of force thereto, a portion of said force-applying assembly being shiftable in response to changes in said sample arising from said heating and application of force thereto; and a device operable to determine said shifting of said force-applying assembly portion.

22. The analyzer of claim 21, said body comprising a tubular member presenting said open end.

23. The analyzer of claim 22, said force-applying assembly comprising:

an elongated, stationary rod received within said tubular member, the end of said rod remote from said open end defining one end of said chamber spaced from said open end; and a drive unit operably coupled with said block for urging said block in a direction to compress said sample between the block and said rod end.

24. The analyzer of claim 23, said drive unit comprising a pair of piston and cylinder assemblies.

25. The analyzer of claim 23, said force-applying assembly further comprising:

an elongated guide rod in axial alignment with said stationary rod, with said block positioned between the guide rod and stationary rod; and an element mounted on said guide rod and axially movable along the length thereof, said element engaging said block, said drive unit coupled with said element.

26. The analyzer of claim 21, said device comprising a displacement transducer.

27. The analyzer of claim 21, said heating assembly comprising a resistance heater adjacent said body.

28. The analyzer of claim 27, said heating assembly further including a passageway for circulation of heating or cooling media.

29. The analyzer of claim 21, said block being selectively shiftable so as to selectively and alternately locate either said first or second segments thereof across said open end.

\* \* \* \* \*